United States Patent
Weissman

(10) Patent No.: US 6,790,465 B2
(45) Date of Patent: Sep. 14, 2004

(54) COMPOSITION AND METHOD FOR TREATING SNORING

(75) Inventor: Glenn H. Weissman, Bradbury, CA (US)

(73) Assignee: Snore-Fix, Inc., San Gabriel, CA (US)

( * ) Notice: Subject to any disclaimer, the term of this patent is extended or adjusted under 35 U.S.C. 154(b) by 5 days.

(21) Appl. No.: 09/973,185

(22) Filed: Oct. 10, 2001

(65) Prior Publication Data

US 2002/0102316 A1 Aug. 1, 2002

Related U.S. Application Data

(60) Provisional application No. 60/250,117, filed on Dec. 1, 2000.

(51) Int. Cl.[7] .................. A61K 35/78; A01N 65/00; C07H 1/00
(52) U.S. Cl. ................. 424/750; 536/123.12
(58) Field of Search ................ 424/750, 725, 424/757, 773, 764; 536/123.12; 435/410

(56) References Cited

U.S. PATENT DOCUMENTS

| | | |
|---|---|---|
| 3,754,925 A | 8/1973 | Kimura et al. |
| 3,822,250 A | 7/1974 | Kimura et al. |
| 4,207,312 A | 6/1980 | Mitsuharu et al. |
| 4,556,557 A | 12/1985 | Reichert |
| 4,774,093 A | 9/1988 | Provonchee |
| 4,820,506 A | 4/1989 | Kleinberg et al. |
| 4,900,722 A | 2/1990 | Williams et al. |
| 5,223,491 A | 6/1993 | Donzis |
| 5,496,558 A | 3/1996 | Napolitano et al. |
| 5,516,765 A * | 5/1996 | Andermann |
| 5,804,211 A | 9/1998 | Robertson et al. |
| 5,886,054 A | 3/1999 | Van Nieuw Amerongen et al. |
| 6,159,459 A | 12/2000 | Hunter et al. |
| 6,187,318 B1 * | 2/2001 | Mitchell et al. |
| 6,210,738 B1 * | 4/2001 | Chen |
| 6,248,390 B1 * | 6/2001 | Stillman |
| 6,284,886 B1 * | 9/2001 | Redmond ............ 536/124 |

FOREIGN PATENT DOCUMENTS

| | | |
|---|---|---|
| EP | 0 137 302 | 9/1984 |
| EP | 0 392 888 A | 10/1990 |
| GB | 2 333 450 A | 7/1999 |
| WO | 00 25588 A | 5/2000 |
| WO | PCT/US01/44817 | 11/2001 |

OTHER PUBLICATIONS

Abstract. XP 002206314. Database WPI Section Ch. Week 200062, Derwent Publications, Ltd., London, GB; AN 2000–645782.

Abstract. XP 002206678. The Merck Index. 1996. Merck Research Laboratories, Whitehouse Station, NJ, p. 1227, paragraph 7276 –p. 1228.

* cited by examiner

*Primary Examiner*—Mike Wityshyn
*Assistant Examiner*—Deborah K. Ware
(74) *Attorney, Agent, or Firm*—McDermott Will & Emery LLP

(57) ABSTRACT

A composition and method are disclosed in which a anti-snoring solution comprising at least one homopolysaccharide is administered to pharyngeal mucous membranes, e.g., soft palate and uvula. The solution preferably includes oat beta glucan and a suitable delivery agent that will hold the active ingredients in solution, and optionally may be combined with essential oil compounds, vitamins, and/or flavoring agents. The solution is preferably administered in the form of a throat spray.

7 Claims, 3 Drawing Sheets

COMPOSITION AND METHOD FOR TREATING SNORING

CROSS REFERENCE TO RELATED APPLICATIONS

This application claims the benefit of U.S. Provisional Application No. 60/250,117, filed Dec. 1, 2000, which is incorporated herein by reference.

FIELD OF THE INVENTION

This application relates to a composition and method useful for treating snoring or the effects thereof.

BACKGROUND OF THE INVENTION

It is estimated that over 50 million individuals snore nightly. The term "snoring" generally refers to a rough or hoarse sound that arises from a person's mouth during sleep. Snoring is believed to be generally caused by the narrowing of the pharyngeal airway such that turbulent airflow during relaxed breathing vibrates the soft parts of the pharyngeal passage, such as the soft palate, the posterior faucial pillars of the tonsils and the uvula. A restricted pharyngeal passageway can occur anatomically. For example, in children, this often is caused by obstruction due to enlarged tonsils or adenoids. In adults, it is not unusual for the narrowing to be caused by obesity. Further anatomical narrowing can be simple a matter of heredity, with some persons being predisposed towards a smaller pharyngeal cross-section. A reduced pharyngeal passageway may also be caused by a lack of muscle tone. Snoring may also be exacerbated by consuming either alcohol or drugs (such as tranquilizers, sleeping pills and antihistamines) prior to bedtime. Smoking can also contribute to the incidence of snoring since cigarettes may irritate the mucus membranes of the upper airway causing swelling and increased mucus production.

Snoring remains a serious problem for a large segment of the population. Snoring is often a significant factor in relationships, causing disturbed sleep patterns, daytime fatigue and hyper-irritability in the non-snoring partner. In more extreme cases, relationship partners sleep in separate bedrooms, which may lead to decreased intimacy, increased resentment and eventually deterioration of the relationship. These factors also cause anxiety and depression that result in failing relationships with friends and co-workers, as well as reduced work performance.

Snoring can indicate a more serious condition and, due to exhaustion resulting from lack of sleep, can cause other problems. For example, an association between snoring and hypertension has been found, and cardiac arrhythmia has been reported during sleep apnea attacks. Sleep apnea is a condition in which the patient stops breathing during sleep. Persons with sleep apnea often snore. Sleep apnea can also be present without snoring. Sleep apnea has been linked to serious medical conditions such as heart disease, hypertension, stroke, obesity, and decreased pulmonary function. In severe cases sleep apnea may even cause death. Not only is the risk of cessation of breathing dangerous, lack of oxygen due to an obstructed pharyngeal passageway deprives the body of sufficient oxygen so that oxygen desaturation arises. Lack of oxygen may cause the brain to rouse the sleeper just enough to take a breath without fully awaking. This may occur hundreds of times a night, with the result that the snorer fails to get sufficient sleep. Moreover, being aroused from deep REM sleep on a repetitive basis may increase heart rate and blood pressure. Thus, snoring may increase the risk of heart attack and stroke, as noted above. Narcolepsy may result from exhaustion, and can cause a lack of attention for the snorer during waking hours, thus reducing productivity and even causing dangerous situations should the exhausted snorer operate machinery or vehicles.

Efforts to control snoring have taken many forms. For example, wrist alarms have been used to rouse a sleeper when the wrist alarm detects the sound of snoring; adhesive nasal strips have been used to help open the nostrils of a sleeper for improved breathing; septum stimulator devices have been used to grip or pinch the nerves of the septum in an effort to improve air flow through the nose; and specially shaped neck pillows have been proposed to realign the spine and relieve muscle stress during sleep. A basic but often unsatisfactory anti-snoring treatment simply involves having an individual sleep in the prone position or on his/her side. Sometimes this is stimulated by sewing a marble or other object into the back of the snorer's clothes. Where an individual is obese, treatment may include a program of weight loss. Anti-snoring sprays containing oils and/or glycerin (a/k/a glycerol or 1,2,3-propanetriol) in combination with water and vitamins have also been developed. Such sprays have largely proven to be ineffective for hydrating mucus due to the short period of contact with the mucus unless repeatedly applied throughout the night. Further, costly intervention (surgery) and mechanical aids (breathing machines) have been tried. For example, costly and invasive surgical methods have been used, such as laser-assisted uvulopalatoplasty which trims and reshapes the uvula and posterior soft palate. This requires three to four procedures spaced four to six weeks apart. In addition, the use of a continuous positive airway pressure (CPAP) generator and face mask has been tried, by which a machine pumps air through a hose and nose/mouth face mask to keep air passages clear. Another example of a treatment device is a custom-made mouth-piece constructed to move the snorer's lower jaw forward, thus opening the airway. Such mouthpieces are generally regarded, however, as being uncomfortable and ineffective.

While numerous snoring management techniques have been described, depending upon the perceived cause of snoring, some of these treatments have proven to be consistently or satisfactorily effective. When snoring is caused or exacerbated by nasal allergy or an upper respiratory tract infection, these conditions may be pharmacologically treated, but, as noted above, this has not proven effective for treating the overall snoring condition. Thus, there remains a long felt but unresolved need for an effective composition and method for treating snoring without the attendant disadvantages of conventionally available compositions and methods.

SUMMARY OF THE INVENTION

It is an object of the present invention to provide a composition and method for preventing, treating or alleviating the effects of snoring in an individual in need thereof.

Another object of the present invention is to make available a composition and method for preventing, treating or alleviating the effects of snoring that is largely present in healthy individuals.

Still another object of the present invention is to provide an anti-snoring composition and method whereby the uvula area of an individual is treated to prevent or reduce the noise effects of snoring while the individual is sleeping.

A further object of the present invention is to provide a composition of the above type that may be topically applied to the soft palate and uvula to reduce or eliminate snoring.

A still further object of the present invention is to provide a composition of the above type that may be easily manufactured.

A still further object of the present invention is to provide a composition of the above type that uses natural active ingredients.

A still further object of the present invention is to provide a composition of the above type that may be applied as a throat spray.

Another object of the present invention is to provide a composition of the above type that may reduce or prevent snoring for hours with a single application.

A still further object of the present invention is to provide a composition of the above type that acts as a vasodilator or in the mucosa to relieve congestion.

Another object of the present invention is to provide a composition of the above type that will reduce swelling of pharyngeal passages and shrink swollen mucous membranes.

A further object of the present invention is to provide a composition of the above type that will cause extended contraction of muscles in the soft palate and uvula areas.

A still further object of the present invention is to provide a composition of the above type that will cause tightening of the mucosa of the uvula and soft palate.

The above and other objects are accomplished by a composition comprising at least one homopolysaccharide (a/k/a homoglycan) as the principle active ingredient, alone or optionally in combination with glycerin as another active ingredient. Application as a throat spray is preferred. Such methods of treatment, their dosage levels and requirements may be selected by those of skill in the art from available methods and techniques that are further described below, are known in the art, or are readily determinable using routine experimentation. Particularly for a throat spray, a flavoring agent, including but not limited to wintergreen, peppermint, cinnamon, lemon oil, eucalyptus or similar oils sorbitol may be used. If used, the flavoring agent is preferably present in the solution in a weight percent substantially within a range of approximately 0.001 to approximately 3, is more preferably substantially within a range of approximately 0.01 to approximately 2, and is most preferably substantially within a range of approximately 0.02 to approximately 1.

Additional aspects, features, embodiments and advantages of the present invention will be set forth, in part, in the description that follows, or may be learned from practicing or using the present invention. The objects and advantages may be realized and attained by means of the features and combinations particularly pointed out throughout this description and the appended claims. It is to be understood that the foregoing general description and the following detailed description are exemplary and explanatory only and are not to be viewed as being restrictive of the invention as claimed.

BRIEF DESCRIPTION OF THE DRAWINGS

The accompanying drawings, which are incorporated in and constitute part of the specification, help to illustrate an embodiment according to the present invention, and, together with the description, serve to exemplify the principles of the present invention.

DETAILED DESCRIPTION OF PREFERRED EMBODIMENTS

Figure 1:
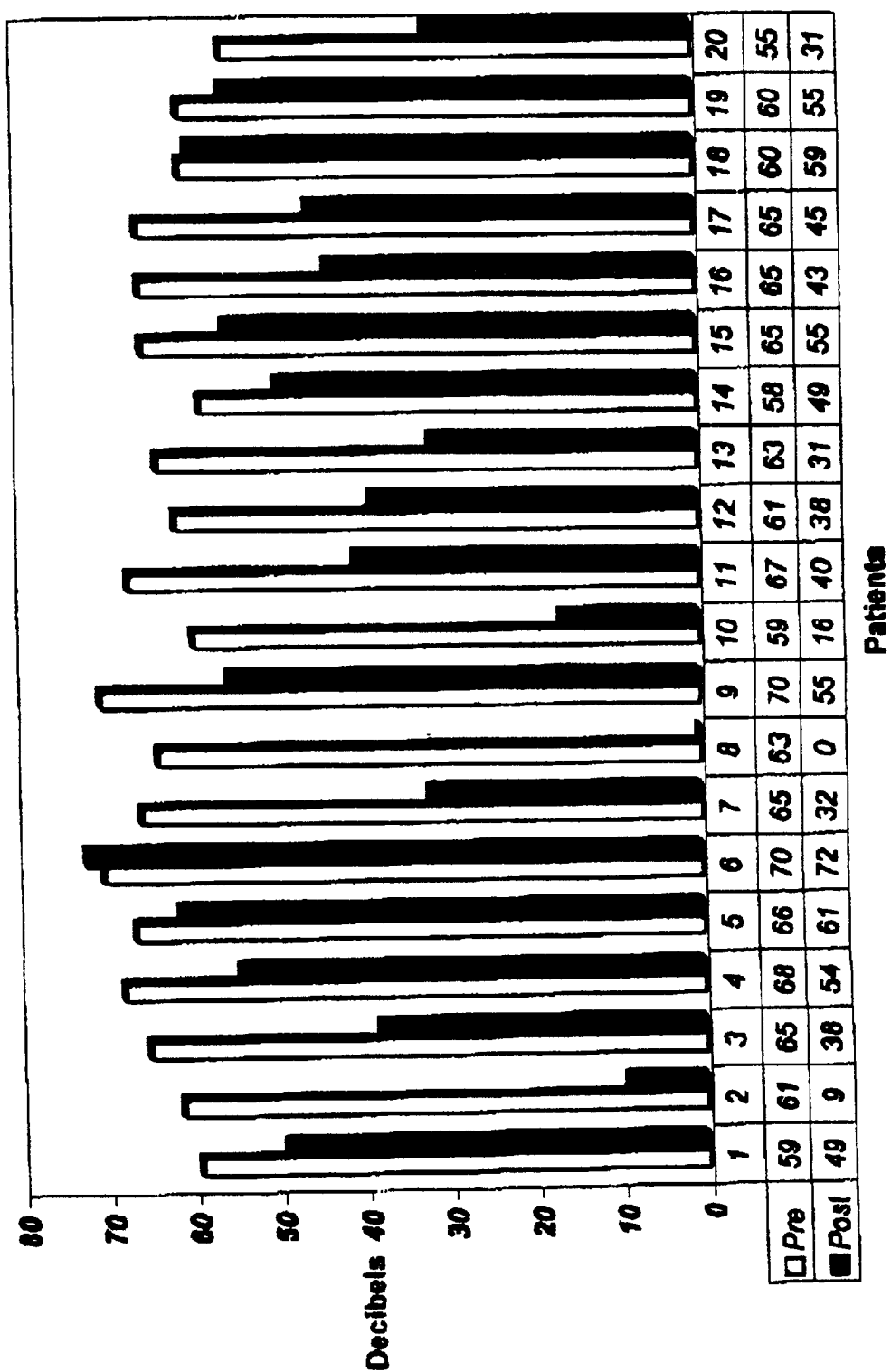
FIG. 1 is a graphical depiction of the results of a study of 20 individuals who suffered from snoring, both before and after use of a composition according to the present invention.

The symptom of snoring is often caused, at least in part, by an inflammation or enlargement of the tissues in the soft palate. The inflammation or enlargement may result from any number of causes; in general, a dynamic complex of cytologic and histologic reactions occur in the affected blood vessels and adjacent tissues in response to an injury or abnormal stimulation caused by physical, chemical or biologic agents. The compositions and methods according to the present invention suppress or eliminate the symptoms of snoring, e.g., noise, by addressing at least some of the root causes thereof.

Compositions of the present invention reduce and/or eliminated noise associated with snoring. While not wishing to be bound by theory, it is believed that the inventive composition works by physiologically coating the back of the throat, thinning out thick oral mucus, and/or increasing blood flow to the uvula to stiffen it, thereby decreasing the vibrations that create snoring noise. The result is a reduction or elimination of noise associated with snoring. There are no known side effects of the inventive composition and it can be used nightly on a repeated basis.

In a preferred embodiment, the anti-snoring composition of the present invention comprises at least one homopolysaccharide. The composition may be administered to the soft palate and uvula to prevent, treat or alleviate the deleterious effects of snoring. Homopolysaccharides are distinct from other polysaccharides (e.g., mucopolysaccharides, a/k/a glycosaminoglycans), which are characterized by having repeating units of only one type of monosaccharide. Examples of the repeating monosaccharide units in preferred homopolysaccharides suitable for use in accordance with the principles of the present invention include, without limitation, glucose, galactose, fructose, xylose, N-acetylglucosamine, etc.

A particularly preferred homopolysaccharide is glucan, e.g., beta 1,3/1,6-glucan, which consists of glucose units. So-called beta glucan may be extracted from animal or botanical sources, however, beta glucan derived from oats ("oat beta glucan") is more preferred. Oat beta-glucan is available from commercial sources.

In a preferred embodiment of the present invention, the homopolysaccharide may be present in the anti-snoring composition of the present invention in an approximate amount of from 0.01% to 50% by weight, more preferably from 0.01% to 25% by weight, and most preferably from 0.01% to 2.5% by weight. Although the anti-snoring composition appears to be effective with glycerin included, glycerin may be absent altogether from the composition, or other components or ingredients may be substituted in place of glycerin.

The inventive composition may also contain one or more members of the group consisting of benzyl alcohol (phenylcarbinol), disodium EDTA, essential oil, eucalyptus oil, sunflower oil (Florasun 90), hybrid sunflower oil, lecithin (a liposome carrier), lemon oil, licorice root extract, peppermint oil, polysorbate 20, polysorbate 80, potassium sorbate, prickly ash extract, purified water (as a solvent), slippery elm extract, sweet almond oil, vitamin A (retinol/retinyl palmitate), vitamin B6 (pyridoxine HCl), vitamin C (ascorbic acid), vitamin E (d-alpha tocopheryl, acetate/tocopherol), and vitamin F (linoleic acid).

Without wishing to be bound by theory, it is believed that the present invention achieves its anti-snoring effects by, inter alia, providing moisture-retention capability to the uvula by adhering to the surface, providing a higher coatability and creating a slippery surface. The composition may directly affect the uvula by shrinking the muscular tissue or fluid tissue of the soft palate and uvula areas. It may even act on alpha-receptors in the mucosa of the respiratory tract, producing vasoconstriction which results in shrinkage of swollen mucous membranes, reduction of tissue, hyperemia, edema and nasal congestion and an increase in nasal airway patency. The inventive composition may also serve as a blocking agent, interfering with the action of histamine, primarily in capillaries surrounding mucous tissues and sensory nerves of nasal and adjacent areas. Also, following oral administration, constriction of blood vessels in the pharyngeal mucosa may relieve nasal congestion. Further, the composition may also antagonize some of the skeletal muscle in the soft palate and uvula, stimulating actions of anti-histamine. It is also believed that the composition may even produce or contribute to extended contractions of the muscles of the soft palate and uvula, lasting several hours. In that regard, smooth muscles, such as those found in the walls of the digestive tract and skeletal muscle, such as those forming the soft palate and uvula, are generally not subject to voluntary control, but are instead controlled by the autonomic nervous system. Smooth muscles contract rather slowly, but can remain contracted for extended periods of time. Muscle contraction begins when the sarcolemma receives an impulse from a motor neuron. The impulse changes the permeability of the sarcoplasmic reticulum throughout the fiber. The reticulum is loaded with calcium and releases the calcium ions into the muscle cytoplasm. A series of activities occur, finally bringing the muscle into its fully shortened state. As long as calcium ions are present and adenosine triphosphate (ATP) is available, the contracted state will hold. Calcium ions appear to be the controlling factor in extended muscle contraction. Thus, it is believed that the present composition may also affect the presence of calcium ions in the muscles, such as by stimulating production or increasing the duration that such ions remain in the muscles of the soft palate and uvula. The solution therefore appears to cause or contribute to extended contractions of the soft palate and uvula, lasting for hours in some individuals.

The active and non-active ingredients of the inventive composition are preferably held in solution by a suitable delivery agent or carrier that may include, without limitation, liposomes, propylene glycol, water and a flavoring agent. Ethyl alcohol may also be present in the solution where the composition components are obtained as extracts suspended in ethyl alcohol. The solution may be administered to the soft palate and uvula, preferably in the form of a throat spray.

The following additional ingredients may be incorporated into the anti-snoring composition of the present invention. As these ingredients are known and used for other purposes, they may be prepared by a person skilled in the art via known methods or may be readily obtained from commercial sources. Each of these ingredients may be preferably present in the composition in a weight percent substantially within a range of approximately 0 to approximately 60, more preferably substantially within a range of approximately 0.001 to approximately 50, and most preferably substantially within a range of approximately 0.01 to approximately 45.

Vitamin A (Retinol or Retinyl Palmitate) has been implicated in protein synthesis, development of skin tissue and mucous membranes, electron transfer reactions and maintenance of the integrity of cell membranes and cell organelles.

Vitamin C (Ascorbic Acid) is a water-soluble vitamin involved in collagen synthesis. Collagen is formed by the hydroxylation of proline to hydroxyproline. Collagen is a protein substance on which the integrity of all fibrous tissue depends. Collagen fibers are critical to the maintenance of bone, cartilage, connective tissue, tooth denton, skin, tendon and blood vessels. Thus, Vitamin C is involved in wound healing. Vitamin C is also a powerful antioxidant. Vitamin C reduces oxidative damage to the cells by fighting off free radicals that are made during the oxidative process. Free radicals can cause many diseases including certain cancers, heart disease and cataracts. In addition, Vitamin C plays a vital role in the immune system, promoting resistance to infection through immunologic activity of leukocytes, the production of interferon, the process of inflammatory reaction, or the integrity of the mucous membranes. Vitamin C also enhances iron absorption in the intestinal tract and aids in transferring iron from plasma transferrin to liver transferrin.

Vitamin E (Tocopherol) may be included in the inventive composition. Vitamin E's primary function is to maintain the integrity of the body's cell membranes. It is the fat-soluble counterpart to Vitamin C, acting as a powerful antioxidant. At the cellular level, it helps stop free radical chain reactions by buffering their assault on cell membranes to prevent significant cell destruction. At the gut level, it enhances the activity of Vitamin A by preventing its oxidation in the intestinal tract. Vitamin E can help improve Vitamin A's absorption, if Vitamin A intake is low, by lowering the rate at which Vitamin A is depleted from the liver. Vitamin A maintains mucus-forming cells and the synthesis of various mucopolysaccharides. Without vitamin A, mucus-forming cells deteriorate and no longer synthesize mucus, a much-needed lubricant used throughout the body.

Vitamin F (Linoleic Acid) is an essential fatty acid that strengthens cell membranes to fortify against the invasion of harmful microorganisms, maintains optimum moisture levels, and increases mucus secretion.

Peppermint oil eliminates bad breath with its pleasant mint flavor and helps clear nasal passages by expelling mucus and improving breathing. It also eliminates gas, bloating, abdominal cramps, relieves headaches and nausea and improves circulation and the production of digestive fluids.

Lemon oil, when included, benefits the respiratory system by improving symptoms associated with catarrh, throat infections and asthma. It is also useful as an antiseptic and antispasmodic.

Eucalyptus oil is an ingredient used in decongestants and mouthwashes. Small amounts are used to relieve many respiratory problems including sinusitis, sinus headache, hay fever, colds, and head congestion. It soothes mucous membranes ensuring ease of breathing.

Slippery Elm Extract swells on contact with water and forms a slimy coating over surfaces and soothes and protects irritated mucous membranes. It also functions as an expectorant.

Licorice Root Extract acts as a secretolytic and expectorant, as confirmed in tests on rabbits.

Polysorbate 20/80 functions as an emulsifier, holding water and oils in suspension, in various foods and supplements.

Potassium Sorbate may be included as a preservative against a wide spectrum of food spoilage microorganisms.

Essential oils that may be included in the anti-snoring composition of the present invention include, without limitation, members selected from the group consisting of α- or β-pinene; α-campholenic aldehyde; α-citronellol; α-isoamyl-cinnamic (e.g., amyl cinnamic aldehyde); α-pinene oxide; α-cinnamic terpinene; α-terpineol (e.g., methods. 1-methyl-4-isopropyl-1-cyclohexen-8-ol); λ-terpinene; achillea; aldehyde C16 (pure); alpha-phellandrene; amyl cinnamic aldehyde; amyl salicylate; anethole; anise; aniseed; anisic aldehyde; basil; bay; benzyl acetate; benzyl alcohol; bergamont (e.g., monardia fistulosa); bitter orange peel; black pepper; borneol; calamus; camphor; cananga oil (e.g., java); cardamom; carnation (e.g., dianthus caryophyllus); carvacrol; carveol; cassia; castor; cedar (e.g., hinoki); cedarwood; chamomile; cineole; cinnamaldehyde; cinnamic alcohol; cinnamon; cis-pinane; citral (e.g., 3,7-dimethyl-2,6-octadienal); citronella; citronellal; citronellol dextro (e.g., 3-7-dimethyl-6-octen-1-ol); citronellol; citronellyl acetate; citronellyl nitrile; citrus unshiu; clary sage; clove (e.g., eugenia caryophyllus); clove bud; coriander; corn; cotton seed; d-dihydrocarvone; decyl aldehyde; diethyl phthalate; dihydroanethole; dihydrocarveol; dihydrolinalool; dihydromyrcene; dihydromyrcenol; dihydromyrcenyl acetate; dihydroterpineol; dimethyl salicylate; dimethyloctanal; dimethyloctanol; dimethyloctanyl acetate; diphenyl oxide; dipropylene glycol; d-limonene; d-pulegone; estragole; ethyl vanillin (e.g., 3-ethoxy-4-hydrobenzaldehyde); eucalyptol (e.g., cineole); eucalyptus citriodora; eucalyptus globulus; eucalyptus; eugenol (e.g., 2-methoxy-4-allyl phenol); evening primrose; fenchol; fennel; ferniol; fish; florazon (e.g., 4-ethyl-α, α-dimethyl-benzenepropanal); galaxolide; geraniol (e.g., 2-trans-3,7-dimethyl-2,6-octadien-8-ol); geraniol; geranium; geranyl acetate; geranyl nitrile; ginger; grapefruit; guaiacol; guaiacwood; gurjun balsam; heliotropin; herbanate (e.g., 3-(1-methyl-ethyl) bicyclo (2, 2, 1) hept-5-ene-2-carboxylic acid ethyl ester); hiba; hydroxycitronellal; i-carvone; i-methyl acetate; ionone; isobutyl quinoleine (e.g., 6-secondary butyl quinoline); isobornyl acetate; isobornyl methylether; isoeugenol; isolongifolene; jasmine; juniper berry; lavender; lemon grass; lemon; lime; limonene; linallol oxide; linallol; linalool; linalyl acetate; linseed; litsea cubeba; 1-methyl acetate; longifolene; mandarin; mentha; menthane hydroperoxide; menthol crystals; menthol laevo (e.g., 5-methyl-2-isopropyl cyclohexanol); menthol; menthone laevo (e.g., 4-isopropyl-1-methyl cyclohexan-3-one); methyl anthranilate; methyl cedryl ketone; methyl chavicol; methyl hexyl ether; methyl ionone; methyl salicylate; mineral; mint; musk ambrette; musk ketone; musk xylol; myrcene; nerol; neryl acetate; nonyl aldehyde; nutmeg (e.g., myristica fragrans); orange (e.g., citrus aurantium dulcis); orris (e.g., iris florentina) root; para-cymene; para-hydroxy phenyl butanone crystals (e.g., 4-(4-hydroxyphenyl)-2-butanone); passion palmarosa oil (e.g., cymbopogon martini); patchouli (e.g., pogostemon cablin); p-cymene; pennyroyal oil; pepper; peppermint (e.g., mentha piperita); perillaldehyde; petitgrain (e.g., citrus aurantium amara); phenyl ethyl alcohol; phenyl ethyl propionate; phenyl ethyl-2-methylbutyrate; pimento berry; pimento leaf; pinane hydroperoxide; pinanol; pine ester; pine needle; pine; pinene; piperonal; piperonyl acetate; piperonyl alcohol; plinol; plinyl acetate; pseudo ionone; rhodinol; rhodinyl acetate; rosalin; rose; rosemary (e.g., rosmarinus officinalis); ryu; sage; sandalwood (e.g., santalum album); sandenol; sassafras; sesame; soybean; spearmint; spice; spike lavender; spirantol; starflower; tangerine; tea seed; tea tree; terpenoid; terpineol; terpinolene; terpinyl acetate; tert-butylcyclohexyl acetate; tetrahydrolinalool; tetrahydrolinalyl acetate; tetrahydromyrcenol; thulasi; thyme; thymol; tomato; trans-2-hexenol; trans-anethole and metabolites thereof; turmeric; turpentine; vanillin (e.g., 4-hydroxy-3-methoxy benzaldehyde); vetiver; vitalizair; white cedar; white grapefruit; and wintergreen, and the like.

The present invention is also directed to a method for treating or alleviating snoring in an individual, the method comprising administering an anti-snoring effective amount of the anti-snoring composition of the present invention to an individual in need thereof. The method encompasses uses of a pharmaceutically acceptable composition in which the active ingredient is present in an amount substantially between about 0.0001–50%, preferably about 0.01–5%, by weight of the mixture.

It is also understood that the inventive composition may be administered in any form and in any manner so long as the active ingredient makes contact with the back of the mouth and results in either reduction or substantial diminution of snoring through prolonged moisturization of the contact area. While a preferred spray formulation is exemplified hereunder, any formulation that is capable of contacting the back of the mouth is within the purview of the present invention, such as mouthwash, lozenge, a squirted liquid spray and so on.

The dosage regimen for the compositions of the present invention will, of course, vary depending upon several factors. In most cases, an individual in need of treatment can readily determine the effective amount of the inventive composition required to prevent, counter or arrest the progress of the condition.

The compositions of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines. In general, water, a suitable oil, saline, aqueous dextrose (glucose), and related sugar solutions and glycols such as propylene glycol or polyethylene glycols are suitable carriers, with water being preferred.

The present invention will be further illustrated in the following, non-limiting examples. The examples are illustrative only and do not limit the claimed invention regarding the materials, conditions, process parameters and the like recited herein.

EXAMPLE 1

Table 1 below shows a preferred formulation of the inventive composition.

TABLE 1

| TRADE NAME | CTFA (INCI) NAME | Approximate Wt % |
|---|---|---|
| Purified Water | Purified Water | 39.90 |
| Potassium Sorbate | Potassium Sorbate | 0.10 |
| Vitamin C | Ascorbic Acid | 0.50 |
| Vitamin B-6 | Pyridoxine HCI | 0.50 |
| Glycerin | Glycerin | 40.00 |
| Florasun 90 | Sunflower Oil | 15.00 |
| Licorice Root Extract | Licorice Root Extract-L.E. | 0.50 |
| Slippery Elm Extract | Slippery Elm Extract-L.E. | 0.50 |
| Vitamin E Oil | dl-Alpha Tocopheryl Acetate | 1.00 |

TABLE 1-continued

| TRADE NAME | CTFA (INCI) NAME | Approximate Wt % |
|---|---|---|
| Oil of Peppermint | Peppermint Oil | 1.00 |
| Oil of Eucalyptus | Eucalyptus Oil | 0.50 |
| Oil of Lemon | Lemon Oil | 0.50 |

EXAMPLE 2

Table 2 shows another preferred formulation of the inventive composition.

TABLE 2

| Ingredient | Function | Approximate Wt % |
|---|---|---|
| Oat Beta Glucan 1.50% | Humectant/Lubricant | 0.01 to 2.50 |
| Glycerin | Humectant/Lubricant | 0.0 to 40.0 |
| Potassium Sorbate | Preservative | 0.01 to 0.1 |
| Lecithin | Nutritional | 0.01 to 2.0 |
| Ascorbic acid | Nutritional | 0.01 to 0.5 |
| Retinyl Palmitate | Nutritional | 0.001 to 0.05 |
| Tocopherol | Nutritional | 0.01 to 0.50 |
| Pyridoxine-HCl | Nutritional | 0.001 to 0.05 |
| Extract of Prickly Ash | Anti-bacterial | 0.01 to 1.0 |
| Extract of Slippery Elm | Astringent | 0.01 to 1.0 |
| Extract of Licorice Root | Anti-inflammatory | 0.01 to 1.0 |
| Linoleic acid | Nutritional | 0.001 to 0.05 |
| Sweet Almond Oil | Lubricant | 0.01 to 2.0 |
| Hybrid Sunflower | Lubricant | 0.01 to 2.0 |
| Peppermint Oil | Flavoring | 0.1 to 2.0 |
| Lemon Oil | Flavoring | 0.1 to 2.0 |
| Eucalyptus Oil | Flavoring | 0.1 to 2.0 |
| PolySorbate 80 | Surfactant | 0.1 to 5.0 |
| Polysorbate 20 | Surfactant | 0.1 to 5.0 |
| Phenylcarbinol | Preservative | 0.01 to 0.2 |
| Disodium EDTA | Preservative | 0.01 to 0.1 |
| Purified Water | Solvent | Balance |

EXAMPLE 3

Objective Study

To evaluate the effectiveness of a composition according to the present invention, a randomized, objective, overnight study was conducted using polysomnographs with sound metered snoring measurements.

Objective Study Methodology

The change in snoring decibel readings was determined by comparing pre- and post-application of a composition as set forth in Table 3, below, to the uvular area of the throat. An "Informed Consent" form was read and signed by each patient prior to being studied. Polysomnogram studies were conducted in conjunction with studying the efficacy of the composition of Table 3. Data were captured from the participant's polysomnograms to evaluate if apnea/hypopnea index (AHI) levels correlate with, and/or impede, the Table 3 composition's effectiveness in regard to reducing and/or eliminating snoring noise.

Professionally trained laboratory technicians were in attendance during the entire length of each participant's study. The Table 3 composition was packaged in coded, unmarked applicator bottles. The technicians were instructed to make no statements to the participants concerning how the product works, and no evaluation of the product was implied to the patient.

The patients slept in their normal sleep positions (except on their stomachs). Thirty minutes after each patient fell asleep, snoring noise was monitored with a digital sound meter. The decibel reading from the snoring noise was documented every 30 minutes for 2 hours thereafter. After 2 hours of monitoring and documenting the sound level of the snoring, the patient was awakened. The patient then sprayed 3 sprays of the Table 3 composition in the back of his or her throat (on the uvula area). The laboratory technician was instructed not to spray the Table 3 composition for the patient. Once the patient sprayed the Table 3 composition, the patient fell back to sleep. All data were documented appropriately on the "Snore Study Data Forms" upon completion of each participant's study.

TABLE 3

| Ingredient | Wt. % | |
|---|---|---|
| Water | 58.82 | wt. % |
| Potassium Sorbate | 0.09 | |
| Oat Beta Glucan 1.50% | 1.00 | |
| Glycerin | 35.00 | |
| Ascorbic acid (Liposome)* | 0.1364 | |
| Retinyl Palmitate (Liposome)* | 0.1364 | |
| Tocopherol Acetate (Liposome)* | 0.1364 | |
| Linoleic Acid (Liposome)* | 0.1364 | |
| Pyridoxine HCl (Liposome)* | 0.1364 | |
| Extract of Prickly Ash (Liposome)* | 0.1364 | |
| Extract of Slippery Elm (Liposome)* | 0.1364 | |
| Extract of Licorice Root (Liposome)* | 0.1364 | |
| Sweet Almond Oil (Liposome)* | 0.1364 | |
| Hybrid Sunflower (Liposome)* | 0.1364 | |
| Lecithin (Liposome)* | 0.1364 | |
| Peppermint Oil | 0.15 | |
| Lemon Oil | 0.15 | |
| Eucalyptus Oil | 0.15 | |
| PolySorbate 80 | 1.50 | |
| Polysorbate 20 | 1.50 | |
| Phenylcarbinol | 0.10 | |
| Disodium EDTA | 0.04 | |

*The total wt. % of the liposome was 1.50%

The Table 3 composition was prepared according to the following general procedure. First water, potassium sorbate, glycerine, and oat beta-glucan were combined at room temperature and warmed to 50° C. to form an aqueous mixture. Next, ascorbic acid, retinyl palmitate, tocopherol acetate, linoleic acid, pyridoxine HCl, extract of prickly ash, extract of slippery elm, extract of licorice root, sweet almond oil, hybrid sunflower, lecithin, peppermint oil, lemon oil, and eucalyptus oil were mixed while warming to 50° C. to form a non-aqueous mixture. Then the aqueous and non-aqueous mixtures were mixed together and the temperature of the mixture was decreased to 40° C. Finally, polysorbate 80, polysorbate 20, phenylcarbinol and disodium EDTA were added with stirring to produce the Table 3 composition, which was then cooled to room temperature.

Results

The study sample had an average age of 43.75 years. Twenty-six patients were enrolled in the study, including 15 men and 5 women who completed the study. Six patients were excluded for the following reasons: one had prolonged latency to sleep, so measurements prior to application of the Table 3 composition were limited; one patient had an apnea index of 98 and was an extremely restless sleeper; three patients did not snore before or after applying the Table 3 composition; one patient did not complete the study. Nineteen of the twenty patients studied reported an improvement in the quality of their sleep following the use of the inventive composition. The average apnea index of all patients was 30.79. The sample group had an overall improvement in snoring by 21.6 decibels. Nineteen of the twenty patients studied showed an objective improvement in decibels of snoring noise following one application (three sprays) of the Table 3 composition.

Table 4 contains the snoring decibel level (dB) data for the twenty (20) patients studied. These data are depicted graphically in FIG. 1.

TABLE 4

| Patient | Before | After |
|---|---|---|
| 1 | 59 dB | 49 dB |
| 2 | 61 | 9 |
| 3 | 64.8 | 37.8 |
| 4 | 67.66 | 54 |
| 5 | 66 | 61 |
| 6 | 69.8 | 71.8 |
| 7 | 65.3 | 31.5 |
| 8 | 63 | 0 |
| 9 | 70 | 55 |
| 10 | 59 | 16 |
| 11 | 66.6 | 40 |
| 12 | 61 | 38 |
| 13 | 63 | 31 |
| 14 | 58 | 49 |
| 15 | 64.8 | 55 |
| 16 | 64.8 | 42.8 |
| 17 | 65 | 45 |
| 18 | 60 | 59 |
| 19 | 60 | 55 |
| 20 | 55 | 31 |

Table 5 shows comparisons of the effectiveness of the Table 3 composition in relation to the participants' genders. Fifteen men had an average of 62 decibels of snoring noise pre-treatment, and 40.5 decibels of noise post-treatment. Five female patients had 53 decibels of noise pre-treatment and 43 decibels post-treatment. Twelve patients with an apnea/hypopnea index (AHI) of 20 or less had a pre-treatment snoring noise of 63.77 decibels and post-treatment snoring noise of 39.4 decibels. Eight patients with an AHI greater than 20.1 had a pre-treatment snoring noise of 62.4 decibels and post-treatment noise of 44.7 decibels. Each patient's AHI was obtained using a polysomnograph. The results revealed that the twelve patients that had AHIs of 20 or less had a pre-treatment snoring noise of 63.77 decibels and post-treatment snoring noise of 39.4 decibels. Eight patients with apnea indexes greater than 20.1 had a pre-treatment snoring decibel level of 62.4 decibels and post-treatment snoring decibel level of 44.7 decibels (Table 6).

Figure 2:
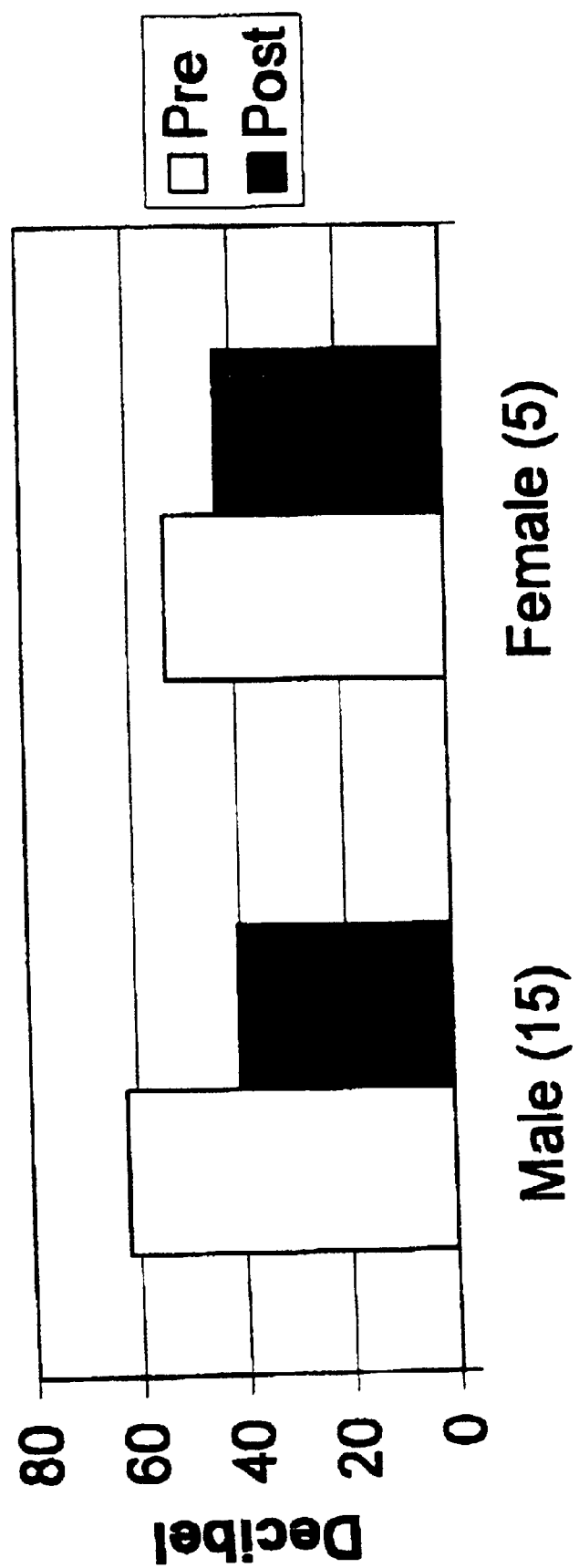
FIG. 2 is a graphical depiction of the results of the study of 20 snorers, wherein the data have been arranged and analyzed by the snorers' genders.

Table 5 shows the decibel (dB) levels according to gender, before and after use of the Table 3 composition. These data are depicted graphically in FIG. 2.

TABLE 5

| | Male (15) | Female (5) |
|---|---|---|
| Before Treatment with the Inventive Composition | 62 dB | 53 dB |
| After Treatment with the Inventive Composition | 40.5 | 43 |

Figure 3:
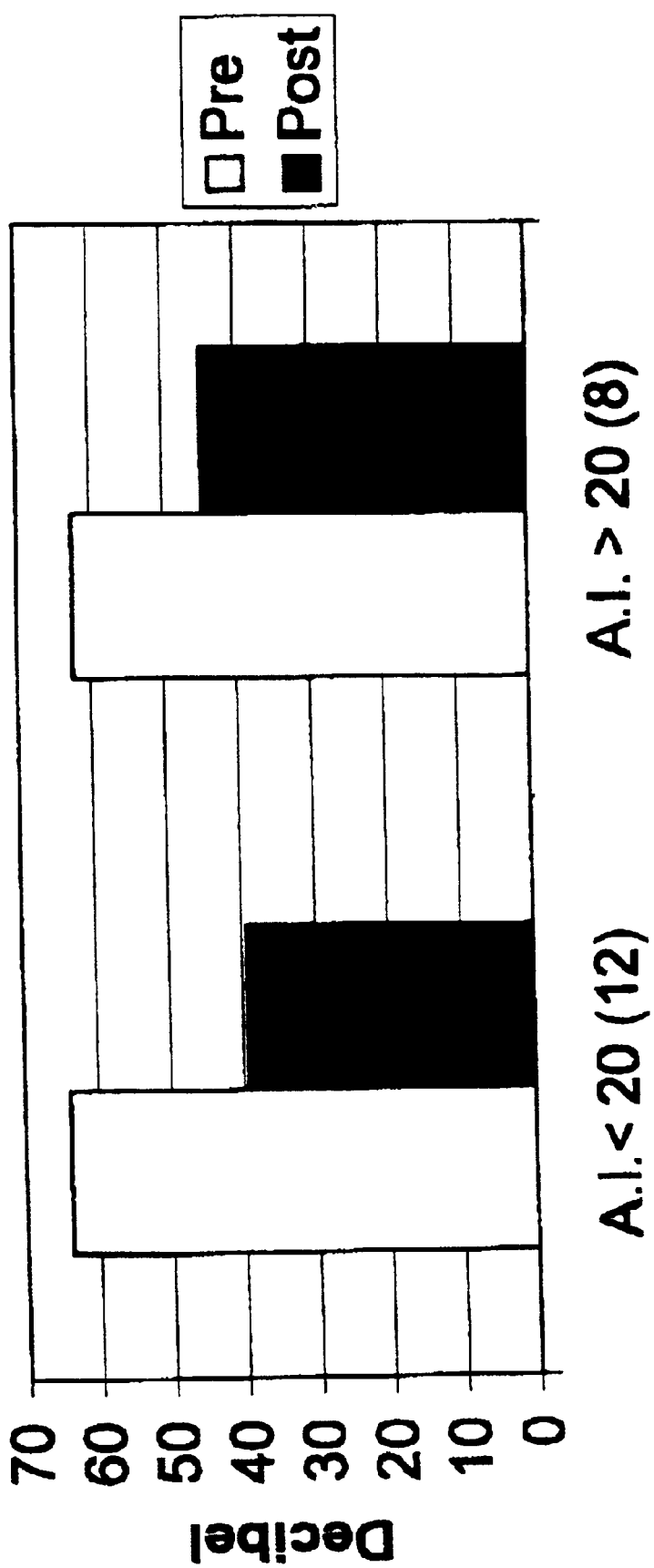
FIG. 3 is a graphical depiction of the results of the study of 20 snorers, wherein the data have been analyzed in view of the apnea indices (A.I.) of the snorers.

Table 6 shows the effectiveness of the Table 3 composition in patients with known sleep apnea. A.I. (apnea index) is equal to the number of respiratory events per hour. These data are graphically depicted in FIG. 3.

TABLE 6

| | A.I. <20 (12) | A.I. >20 (8) |
|---|---|---|
| Before Treatment with the Inventive Composition | 63.77 dB | 62.4 dB |
| After Treatment with the Inventive Composition | 39.4 | 44.7 |

There were no reports of negative reactions to the Table 3 composition and there were no interactions between the Table 3 compositions and any drugs. All ingredients contained in the Table 3 composition are generally recognized as safe (GRAS) by the food and drug administration.

EXAMPLE 4

Subjective Study

The Table 3 composition was further evaluated according to the following protocol.

Subjective Study Methodology

The object of the subjective study was to determine, by a written questionnaire, if participants experienced any known side effects or negative reactions while using the Table 3 composition. In addition, test subjects were asked how effective the inventive composition was at reducing their snoring noise level. Heights and weights also were taken so that a correlation could be studied between each patient's body mass index (BMI, i.e. the subject's mass in kilograms divided by the square of the subject's height in meters) and the inventive composition's efficacy. Numerous studies have linked sleep apnea and snoring with obesity (increased BMI of 30 or greater).

Test Planning and Patients

Test preparation: The test preparation, i.e. the Table 3 composition, contains natural ingredients, including vitamins, essential oils and oat beta glucan.

Dosage: Two to three sprays in the back of the throat just before bedtime. Do not eat or drink 30 minutes before using.

The study and size of sample: This is a randomized study where subjective opinions and experiences were offered. The study pool included 50 male and 10 female participants.

Criteria for inclusion: Participants had varying degrees of snoring, heights, and weights. Participants were also asked if they had ever been diagnosed with sleep apnea by their physicians. All participants were included in the study, regardless of these factors.

Test Plan: Participants tested the Table 3 composition. Questionnaires were sent to 100 adults. The participants were told what the product was. The questionnaire asked that the participants have their bedmate, if applicable, answer the questions with them, so that the highest degree of accuracy for each question could be obtained.

The questionnaire included the following questions:
1. Age, height, weight, sex?
2. (a) Before using the Table 3 composition, how would you rate the loudness of your snoring (according to your bed mate or other members of your household, if applicable)? Please answer on a scale from 1 to 10, 1 being silent, 5 being "wakes your bedmate," and 10 being "wakes the neighbors."
   (b) Does your snoring cause you and your bed mate (if applicable) to sleep in separate beds?
   (c) Does you snoring cause you to have less energy during the day?
   (d) Does your snoring case you to have less interest in sex with your loved one?

(e) Please rate how using the Table 3 composition has reduced the noise level caused by your snoring? Please answer on a scale from 1 to 10, 1 being "noise level unchanged," 5 being "reduced noise," 10 being "eliminated noise."

(f) Has using the Table 3 composition reduced the frequency of your snoring?

(1) Answers: Yes! I no longer snore;

(2) I snore 1–2 nights per week;

(3) I snore 3–4 nights per week;

(4) No, I snore more than 5 night per week.

(g) Has using the Table 3 composition helped you and your bedmate get more restful sleep?

(h) How would you describe the taste of the Table 3 composition? Pleasant or non-pleasant tasting?

(i) Have you ever had a sleep study done by your doctor?

(j) Have you ever been diagnosed with a sleep disorder?

Results/Effectiveness

Fifty-eight participants (97%) showed reduced snoring noise with the Table 3 Composition. Two participants showed no change in noise reduction. Participants were asked to rate the change in their snoring noise level after the use of the Table 3 composition by referring to a numerical scale from 1 to 10; 1 being noise level unchanged, 5 being reduced noise, and 10 being eliminated the noise. The total mean score from all participants was 7.07, which revealed that a majority of the participants experienced more than a reduction in their snoring noise. The mode was 9 and the median was 1 through 10. There were no reactions or drug to drug interactions reported.

Participants' body mass indexes (BMIs) were shown to have no correlation to the effectiveness that the Table 3 composition had on snoring noise reduction. The BMI values ranged from 19.2 to 37.7 (see Table 7). The mean BMI was 29.8, which is considered overweight and increases a person's risk of health disease. A BMI of 30 or greater is considered obese and increases the risks of acquiring numerous health conditions.

Sixty-three percent (63%) of the Participants had a BMI between 25 and 29.9, which is overweight. Twenty-five percent (25%) were obese and only twelve percent were at a healthy BMI. The sixty participants who participated experienced a positive reduction in their snoring noise, regardless of their BMI.

Snoring occurs more frequently in persons who are overweight and obese. There is a smaller population of people that experiences snoring at a healthy BMI. In our study, the Table 3 composition reduced snoring decibel levels in persons with high and low BMIs. Only two participants found no reduction in their snoring decibel level when using the Table 3 composition. Consequently, their BMIs were 29.6 and 30.1, which falls under the category of overweight and obese, respectively.

Eighty percent of participants experienced between a score of 5 (reduced the noise) to 10 (eliminated the noise) in the reduction of their snoring noise. Seventeen percent actually experienced a complete elimination of their snoring noise.

Table 7 shows the participants' sex, height, weight, BMI, and snoring reduction scores. The snoring reduction score is based on a scale from 1 to 10, 1 being "noise level unchanged," 5 being "reduced noise," 10 being "eliminated snoring noise."

TABLE 7

| Sex | Weight (lb.) | Height | BMI (kg/m$^2$) | Snore Score |
|---|---|---|---|---|
| M | 222 | 5'10" | 31.9 | 7 |
| M | 190 | 5'11" | 28.5 | 7 |
| F | 180 | 5'3" | 31.9 | 5 |
| M | 175 | 6'0" | 37.7 | 7 |
| M | 216 | 5'10" | 28.7 | 9 |
| M | 278 | 6'0" | 25.1 | 6 |
| M | 200 | 5'10" | 25.8 | 6 |
| M | 185 | 6'0" | 28.4 | 9 |
| M | 175 | 5'9" | 30.5 | 4 |
| M | 187 | 5'8" | 28.7 | 7 |
| M | 196 | 5'7" | 23.1 | 9 |
| M | 200 | 5'10" | 37.3 | 10 |
| M | 175 | 6'1" | 34.4 | 10 |
| M | 280 | 5'10" | 27.5 | 2 |
| M | 247 | 5'11" | 29.6 | 10 |
| M | 192 | 5'10" | 27.0 | 10 |
| M | 212 | 5'11" | 30.1 | 1 |
| M | 188 | 5'10" | 28.4 | 9 |
| M | 210 | 5'10" | 27.5 | 8 |
| M | 192 | 5'9" | 28.4 | 9 |
| M | 182 | 5'10" | 27.5 | 9 |
| M | 178 | 5'9" | 26.3 | 9 |
| M | 210 | 6'0" | 28.5 | 8 |
| M | 187 | 5'10' | 26.8 | 9 |
| M | 200 | 5'11" | 27.9 | 9 |
| M | 198 | 6'0" | 26.9 | 9 |
| M | 205 | 6'2" | 26.3 | 7 |
| M | 235 | 6'0" | 31.9 | 8 |
| M | 180 | 5'7" | 28.2 | 5 |
| M | 220 | 6'2" | 28.2 | 5 |
| M | 260 | 5'10" | 37.3 | 7 |
| M | 250 | 5'11" | 34.9 | 5 |
| F | 119 | 5'6" | 19.2 | 4 |
| M | 190 | 5'10" | 27.3 | 10 |
| M | 200 | 5'10" | 28.7 | 8 |
| M | 165 | 5'6" | 26.6 | 4 |
| F | 196 | 5'8" | 29.6 | 1 |
| M | 240 | 5'11' | 33.5 | 7 |
| M | 215 | 6'0" | 29.2 | 7 |
| F | 150 | 5'8" | 22.8 | 10 |
| F | 135 | 5'6" | 21.8 | 4 |
| M | 215 | 6'2" | 27.6 | 7 |
| F | 158 | 5'8" | 24 | 10 |
| M | 220 | 6'4" | 26.8 | 9 |
| M | 190 | 5'7" | 29.8 | 4 |
| F | 200 | 5'9" | 29.5 | 7 |
| M | 192 | 5'11" | 26.8 | 10 |
| M | 260 | 6'11" | 34.3 | 8 |
| M | 260 | 6'0" | 35.3 | 2 |
| M | 185 | 5'10" | 26.5 | 9 |
| F | 180 | 5'10" | 23 | 5 |
| M | 190 | 5'10" | 27.3 | 9 |
| F | 140 | 5'3" | 24.8 | 8 |
| M | 210 | 6'0" | 28.5 | 8 |
| M | 195 | 6'0" | 26.4 | 7 |
| M | 190 | 5'7" | 29.8 | 7 |
| M | 180 | 5'8" | 27.4 | 10 |
| F | 200 | 5'6" | 33.3 | 3 |
| M | 200 | 5'10" | 28.7 | 10 |
| M | 180 | 5'10" | 25.8 | 5 |

Discussion

After analyzing the detailed results and the study's findings, it can be stated that the Table 3 composition reduces and/or eliminates the noise associated with snoring, as witnessed by several people who suffer from snoring and their bedmates.

The findings show that one application (two to three sprays) of the Table 3 composition, just before bedtime, can greatly improve the snorers' and their bedmates' sleep.

The Table 3 composition was shown to have no known side effects. The effectiveness of the inventive composition does not appear to correlate with a person's BMI, whether high or low. The Table 3 composition was developed to be used nightly and offers a simple, easy, inexpensive treatment for snoring noise. People who have been diagnosed with, or suspect, sleep apnea should seek medical treatment immediately. The Table 3 composition is not intended to treat a medical condition, and in fact, could mask the signs of sleep apnea in known patients. This study was done to prove the effectiveness of the Table 3 composition on a subjective level only. Since snoring is an audiological irritant to the snorer's bedmate, subjective opinions are valuable for evaluating the effectiveness of snoring therapies.

The foregoing examples are presented for illustrative purposes only, and are not in any way intended to limit the scope of the present invention. A person having skill in the art will recognize that other embodiments are within the scope of the present invention, and will be able to employ the foregoing description to practice further embodiments within the scope of the present invention. All references cited herein are expressly incorporated by reference.

What is claimed is:

1. A method for treating snoring in a subject, the method comprising:

orally administering to a subject in need thereof an effective amount of an anti-snoring composition consisting essentially of: approximately 0.01 to 2.5 wt % of oat beta glucan, glycerin present in an amount of no more than approximately 40 wt % and water.

2. The method of claim 1 wherein the anti-snoring composition consists essentially of about 1 wt % of oat beta glucan and about 35 wt % of glycerin.

3. The method of claim 1 wherein the anti-snoring composition further consists essentially of: approximately 0.01 to 2 wt % of at least one nutritional ingredient; approximately 0.01 to 1 wt % of at least one antibacterial; approximately 0.01 to 1 wt % of at least one astringent; approximately 0.01 to 1 wt % of at least one anti-inflammatory; approximately 0.01 to 2 wt % of at least one essential oil; approximately 0.01 to 10 wt % of at least one surfactant; and approximately 0.01 to 0.4 wt % of at least one preservative.

4. The method of claim 3 wherein the at least one antibacterial is extract of prickly ash, the at least one astringent is extract of slippery elm; and the at least one anti-inflammatory is extract of licorice root.

5. A method for treating snoring in a subject, the method comprising:

orally administering to a subject in need thereof an effective amount of an anti-snoring composition consisting essentially of approximately 0.01 to 2.5 wt % of oat beta glucan, glycerin present in an amount of no more than approximately 40 wt % and the following ingredients:

| Ingredient | Approximate Wt % |
| --- | --- |
| Potassium Sorbate | 0.01 to 0.1 |
| Lecithin | 0.01 to 2.0 |
| Ascorbic acid | 0.01 to 0.5 |
| Retinyl Palmitate | 0.001 to 0.05 |
| Tocopherol | 0.01 to 0.50 |
| Pyridoxine-HCl | 0.001 to 0.05 |
| Extract of Prickly Ash | 0.01 to 1.0 |
| Extract of Slippery Elm | 0.01 to 1.0 |
| Extract of Licorice Root | 0.01 to 1.0 |
| Linoleic acid | 0.001 to 0.05 |
| Sweet Almond Oil | 0.01 to 2.0 |
| Hybrid Sunflower | 0.01 to 2.0 |
| Peppermint Oil | 0.1 to 2.0 |
| Lemon Oil | 0.1 to 2.0 |
| Eucalyptus Oil | 0.1 to 2.0 |
| PolySorbate 80 | 0.1 to 5.0 |
| Polysorbate 20 | 0.1 to 5.0 |
| Phenylcarbinol | 0.01 to 0.2 |
| Disodium EDTA | 0.01 to 0.1 |
| Purified Water | Balance |

6. A method for treating snoring in a subject, the method comprising:

orally administering to a subject in need thereof an effective amount of an anti-snoring composition consisting of: approximately 0.01 to 2.5 wt % of oat beta glucan; glycerin present in an amount of no more than approximately 40 wt %; approximately 0.01 to 2 wt % of at least one nutritional ingredient; approximately 0.01 to 1 wt % of at least one antibacterial; approximately 0.01 to 1 wt % of at least one astringent; approximately 0.01 to 1 wt % of at least one anti-inflammatory; approximately 0.01 to 2 wt % of at least one essential oil; approximately 0.01 to 10 wt % of at least one surfactant; approximately 0.01 to 0.4 wt % of at least one preservative; and the balance water.

7. The method of claim 6 wherein the anti-snoring composition consists of about 1 wt % of oat beta glucan and about 35 wt % of glycerin.

* * * * *